US00PP25216P2

(12) United States Plant Patent
Beekenkamp

(10) Patent No.: US PP25,216 P2
(45) Date of Patent: Jan. 6, 2015

(54) ***BEGONIA* PLANT NAMED 'BKPBEEVR'**

(50) Latin Name: *Begonia hiemalis*
Varietal Denomination: BKPBEEVR

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 85 days.

(21) Appl. No.: 13/815,610

(22) Filed: Mar. 11, 2013

(51) Int. Cl.
*A01H 5/00* (2006.01)

(52) U.S. Cl.
USPC ..... Plt./349

(58) Field of Classification Search
USPC ..... Plt./349
See application file for complete search history.

*Primary Examiner* — Annette Para
(74) *Attorney, Agent, or Firm* — C. A. Whealy

(57) ABSTRACT

A new and distinct cultivar of *Begonia* plant named 'BKPBEEVR', characterized by its upright, somewhat outwardly spreading and mounded plant habit; freely basal branching habit; dark green-colored leaves; uniform and freely flowering habit; and double flowers that are dark red in color.

2 Drawing Sheets

Botanical designation: *Begonia hiemalis.*
Cultivar denomination: 'BKPBEEVR'.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'BKPBEEVR'.

The new *Begonia* plant is a product of a planned breeding program conducted by the Inventor in Maasdijk, The Netherlands. The objective of the breeding program was to develop new freely branching and freely flowering *Begonia* plants with attractive flower color.

The new *Begonia* plant originated from a cross-pollination made by the Inventor in July, 2010 of a proprietary selection of *Begonia hiemalis* identified as code number 6501140, not patented, as the female, or seed, parent with a proprietary selection of *Begonia hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in December, 2010.

Asexual reproduction of the new *Begonia* plant by tip cuttings in a controlled greenhouse environment in Maasdijk, The Netherlands since March, 2011 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEVR'.

These characteristics in combination distinguish 'BKPBEEVR' as a new and distinct *Begonia* plant:

1. Upright, somewhat outwardly spreading and mounded plant habit.
2. Freely basal branching habit.
3. Dark green-colored leaves.
4. Uniform and freely flowering habit.
5. Double flowers that are dark red in color.

Plants of the new *Begonia* can be compared to plants of the female parent selection. Plants of the new *Begonia* differ primarily from plants of the female parent selection in the following characteristics:

1. Plants of the new *Begonia* have lighter-colored leaves than plants of the female parent selection.
2. Plants of the new *Begonia* have smaller flowers than plants of the female parent selection.
3. Flower tepals of plants of the new *Begonia* are dark red in color whereas flower tepals of plants of the female parent selection are orange in color.

Plants of the new *Begonia* can be compared to plants of the male parent selection. Plants of the new *Begonia* differ primarily from plants of the male parent selection in the following characteristics:

1. Plants of the new *Begonia* have darker-colored leaves than plants of the male parent selection.
2. Plants of the new *Begonia* have double flowers whereas plants of the male parent selection have single flowers.
3. Flower tepals of plants of the new *Begonia* are dark red in color whereas flower tepals of plants of the male parent selection are pink in color.

Plants of the new *Begonia* can be compared to plants of the *Begonia* 'Baladin', not patented. In side-by-side comparisons conducted in Maasdijk, The Netherlands, plants of the new *Begonia* differed from plants of 'Baladin' in the following characteristics:

1. Plants of the new *Begonia* had darker green-colored leaves than plants of 'Baladin'.

2. Plants of the new *Begonia* had smaller flowers with fewer tepals than plants of 'Baladin'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEEVR' grown in a container.

The photograph on the second sheet are close up views of typical flower buds, flowers and leaves of 'BKPBEEVR'.

DETAILED BOTANICAL DESCRIPTIONS

Plants used for the aforementioned photographs and following observations and measurements were grown in 12-cm containers during the winter in a glass-covered greenhouse in Maasdijk, The Netherlands. During the production of the plants, day temperatures ranged from 19° to 20° C., night temperatures ranged from 18° to 19° C. and light levels averaged 6,000 lux. Plants were eleven weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBEEVR'.

Parentage:

*Female, or seed, parent*.—Proprietary selection of *Begonia hiemalis* identified as code number 6501140, not patented.

*Male, or pollen, parent*.—Proprietary selection of *Begonia hiemalis* identified as code number 6500604, not patented.

Propagation:

*Type*.—By tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; light brown in color; plants of the new *Begonia* have not been observed to form tubers.

*Rooting habit*.—Moderate branching; medium density.

Plant description:

*Plant and growth habit*.—Upright, somewhat outwardly spreading and mounded plant habit; plant shape roughly obovate to globular; freely basal branching with about six basal branches per plant; moderately vigorous growth habit.

*Plant height*.—About 29.3 cm.

*Plant width*.—About 30.9 cm.

*Lateral branch description*.—Length: About 18.9 cm. Diameter: About 8 mm. Internode length: About 2.6 cm. Texture: Sparsely pubescent. Aspect: Upright to about 30° from the vertical. Color, developing: Close to 146B and 152C. Color, fully developed: Close to 146A.

*Leaf description*.—Arrangement: Alternate, simple. Length: About 12.1 cm. Width: About 9.3 cm. Shape: Roughly ovate, unequal. Apex: Broadly acute. Base: Oblique to hastate. Margin: Bi-serrate to bi-crenate. Texture, upper surface: Smooth, glabrous; velvety. Texture, lower surface: Sparsely pubescent along margins and main veins. Venation pattern: Palmate. Color: Developing leaves, upper surface: Slightly darker than between 146A and 147A. Developing leaves, lower surface: Close to 182B. Fully expanded leaves, upper surface: Darker than between 147A and N189A; venation, close to 143A. Fully expanded leaves, lower surface: Close to 147B tinged with close to 182B; venation, close to 146B to 146C. Petioles: Length: About 5.6 cm. Diameter: About 5 mm. Texture, upper and lower surfaces: Pubescent. Color, upper surface: Close to 146A tinged with close to 152B. Color, lower surface: Close to 146B to 146C tinged with close to 152B.

Flower description:

*Flowering habit*.—Fully double rotate flowers arranged in axillary compound cymes; flowers sterile; freely flowering habit with about nine flowers per cyme and about 380 flowers developing per plant; flowers face upright to outwardly.

*Fragrance*.—None detected.

*Natural flowering season*.—Plants begin flowering about 65 days after planting; long flowering period, plants flower freely and continuously from spring into the autumn in The Netherlands.

*Flower longevity*.—Individual flowers last about ten days on the plant; flowers not persistent.

*Inflorescence height*.—About 12 cm.

*Inflorescence diameter*.—About 12.1 cm.

*Flower diameter*.—About 5.3 cm.

*Flower height*.—About 2.4 cm.

*Flower buds*.—Length: About 1.8 cm. Diameter: About 7 mm to 20 mm. Shape: Orbicular, flattened. Color: Close to N34A.

*Tepals*.—Quantity per flower and arrangement: Two, opposite. Length: About 2.8 cm. Width: About 2.8 cm. Shape: Orbicular. Apex: Rounded. Margin: Entire. Texture, upper surface: Smooth, glabrous; velvety. Texture, lower surface: Smooth, glabrous; slightly velvety. Color: When opening, upper surface: Close to 45B and 46B. When opening, lower surface: Close to between N34A and N34C. Fully opened, upper surface: Close to 45B; towards the base, close to 45C; color does not fade with development. Fully opened, lower surface: Close to 42A; color does not fade with development.

*Tepaloids*.—Quantity per flower and arrangement: About 16 in multiple whorls. Length: About 2.2 cm. Width: About 1.7 cm. Shape: Obovate. Apex: Rounded. Margin: Entire. Texture, upper surface: Smooth, glabrous; velvety. Texture, lower surface: Smooth, glabrous; slightly velvety. Color: When opening and fully opened, upper surface: Close to 45B; color does not fade with development. When opening and fully opened, lower surface: Close to 45C; color does not fade with development.

*Peduncles*.—Length: About 12.1 cm. Diameter: About 3 mm to 4 mm. Angle: About 30° from branch axis. Strength: Flexible, bending with the weight of the flowers. Texture: Smooth, glabrous. Color: Close to 152A.

*Pedicels*.—Length: About 2.2 cm. Diameter: About 2 mm. Angle: About 45° from the peduncle axis.

Strength: Flexible, bending with the weight of the flowers. Texture: Densely pubescent. Color: Close to 177C.

*Reproductive organs*.—Androecium: Not observed on plants of the new *Begonia*. Gynoecium: Not observed on plants of the new *Begonia*.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'BKPBEEVR' as illustrated and described.

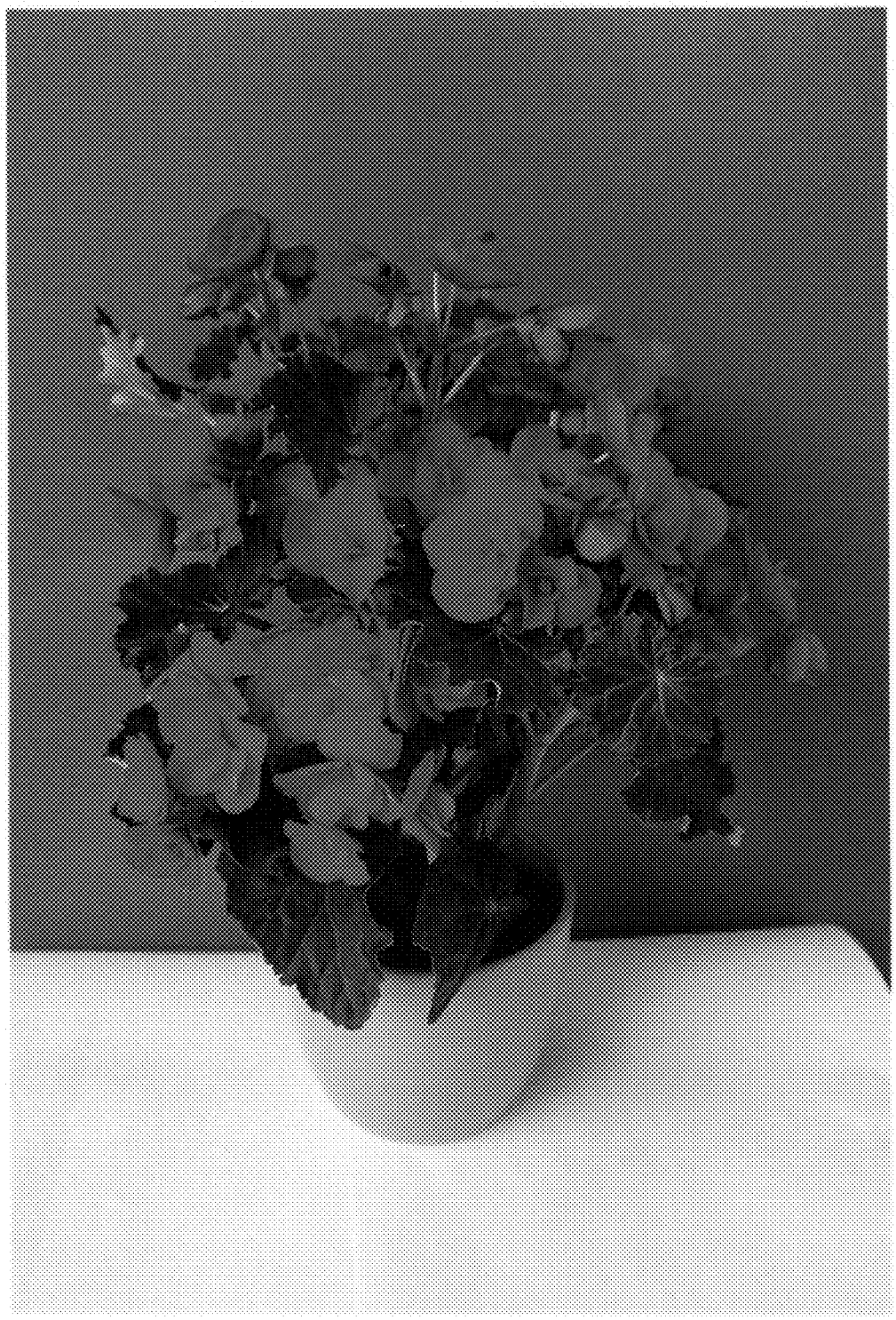

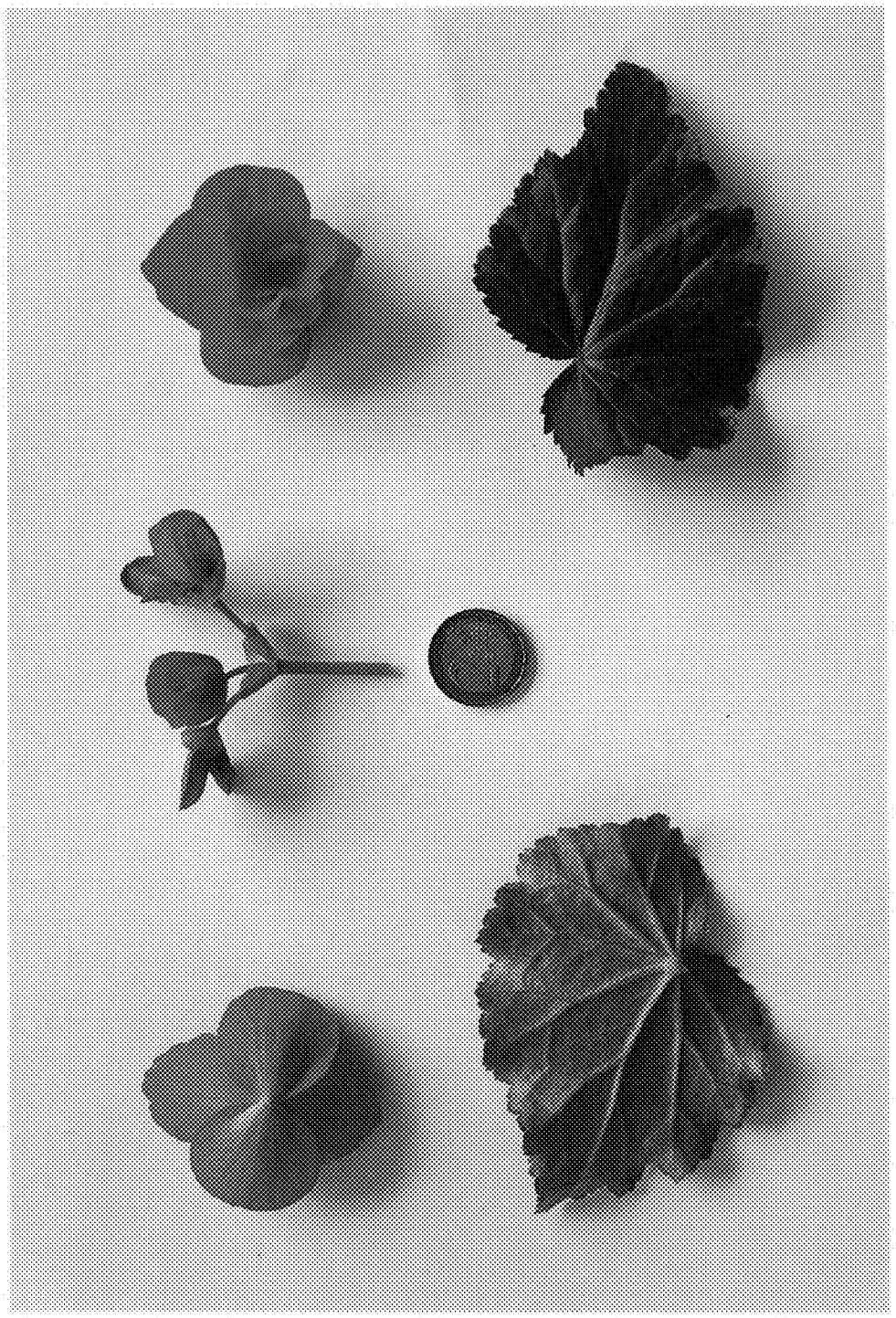

* * * * *